(12) United States Patent
McKenry

(10) Patent No.: US 10,455,839 B2
(45) Date of Patent: Oct. 29, 2019

(54) PRE-PLANT BIOCIDE USES OF AQUEOUS CYANAMIDES

(71) Applicant: METBRO DISTRIBUTING LP, Fresno, CA (US)

(72) Inventor: Michael McKenry, Fresno, CA (US)

(73) Assignee: METBRO DISTRIBUTING LP, Fresno, CA (US)

(*) Notice: Subject to any disclaimer, the term of this patent is extended or adjusted under 35 U.S.C. 154(b) by 0 days.

(21) Appl. No.: 15/773,742

(22) PCT Filed: Nov. 7, 2016

(86) PCT No.: PCT/US2016/060842
§ 371 (c)(1),
(2) Date: May 4, 2018

(87) PCT Pub. No.: WO2017/083231
PCT Pub. Date: May 18, 2017

(65) Prior Publication Data
US 2018/0317497 A1    Nov. 8, 2018

Related U.S. Application Data

(60) Provisional application No. 62/252,833, filed on Nov. 9, 2015.

(51) Int. Cl.
| | | |
|---|---|---|
| A01N 59/24 | (2006.01) | |
| C05C 7/00 | (2006.01) | |
| A01N 31/02 | (2006.01) | |
| A01N 25/02 | (2006.01) | |

(52) U.S. Cl.
CPC ............ *A01N 59/24* (2013.01); *A01N 25/02* (2013.01); *A01N 31/02* (2013.01); *C05C 7/00* (2013.01)

(58) Field of Classification Search
CPC .................................................. A01N 59/24
See application file for complete search history.

(56) References Cited

U.S. PATENT DOCUMENTS

| | | |
|---|---|---|
| 3,295,926 A | 1/1967 | Henry et al. |
| 4,562,289 A | 12/1985 | Hajek et al. |
| 5,566,627 A | 10/1996 | Pryor |
| 5,586,728 A | 12/1996 | McKenry |
| 6,458,747 B1 | 10/2002 | Kulik |
| 6,720,352 B1 | 4/2004 | Rodriguez-Kabana |
| 8,021,648 B2 * | 9/2011 | Rodriguez-Kabana ...... A01N 59/24 424/40 |
| 8,052,985 B2 | 11/2011 | Gorden et al. |
| 9,179,671 B2 | 11/2015 | Kiguchi et al. |
| 2007/0092581 A1 | 4/2007 | Rodriguez-Kabana |
| 2008/0214679 A1 | 9/2008 | Rodriguez-Kabana et al. |
| 2011/0218104 A1 | 9/2011 | Rodriguez-Kabana |
| 2012/0183354 A1 | 7/2012 | Redmile-Gordon et al. |

FOREIGN PATENT DOCUMENTS

| | | |
|---|---|---|
| CA | 2337536 A1 | 1/2000 |
| WO | 2007050641 A2 | 5/2007 |
| WO | 2009042567 A1 | 4/2009 |
| WO | 2012050234 A2 | 4/2012 |
| WO | 2014152943 A1 | 9/2014 |
| WO | 2014/169175 A1 | 10/2014 |

OTHER PUBLICATIONS

International Searching Authority At the United States Patent and Trademark Office, International Search Report and Written Opinion for International Application No. PCT/US2016/060842, dated Mar. 29, 2017, 10 pages.
Or, et al., Timing of Hydrogen Cyanamide Application to grapevine Buds, Vitis, 1999, 6 pages, vol. 38.
Brouwer, et al., Irrigation Water Management: Training Manual No. 1—Introduction to Irrigation, Chapter 2: Soil and Water, 1985, pp. 1-23.

(Continued)

*Primary Examiner* — Brian J Davis
(74) *Attorney, Agent, or Firm* — Mintz Levin Cohn Ferris Glovsky and Popeo, P.C.

(57) ABSTRACT

Hydrogen cyanamide (HyCyn) is a product derived from calcium cyanamide. Three decades ago HyCyn became commercially available as a plant growth regulator. Sprayed on dormant plants, it provides uniform bud-break. This present invention provides repeatable methods for using aqueous HyCyn, and other similar water-soluble low molecular weight cyanamide or nitrile containing compounds, as stand-alone biocides. Qualities include: safer delivery to field settings, fewer environmental impacts and predictable plant growth improvement. HyCyn with its systemic qualities can act as a fertilizer, desiccant, nematicide, fungicide, herbicide, growth regulator and an agent of enzyme inactivation. These biocidal and other effects appear to be a result of double or triple bonds connecting carbon with nitrogen, and therefore it is expected that other water-soluble low molecular weight compounds having carbon-nitrogen double or triple bonds can act similarly. Today's improved irrigation methods will replace soil fumigation in many settings. All its metabolites, properly delivered, make plants grow better.

20 Claims, 27 Drawing Sheets

(56) References Cited

OTHER PUBLICATIONS

Diercks, et al., Uber die Fungitoxische Wirkung des Cyanamids Gegen Cercosporella Herpotrichoides, Die Naturwissenschaften, 1964, pp. 118-119.
European Patent Office, Extended Search Report for EP14782359.5, dated Oct. 20, 2016, 7 pages.
International Searching Authority at the United States Patent and Trademark Office, International Search Report for PCT/US2014/033743, dated Aug. 22, 2014, 8 pages.
McKenry, The Replant Problem and Its Management, 1999, pp. 1-33.
Ministry of Agriculture, Soil Water Storage Capacity and Available Soil Moisture, Water Conservation Factsheet 619.000-1, Agdex: 550, Jun. 2015, 4 pages.
Rodriguez-Kabana, Pesticidal Properties of Hydrogen Cyanamide: a Nonfumigant Water-soluble Compound, 2008 Annual International Research Conference on Methyl Bromide Alternatives and Emissions Reductions, Orlando, Florida, 2008, 62 pages.
Skoog, Chemical Control of Weeds in Burley Tobacco Plant Beds, University of Tennessee Agricultural Experiment Station, Jul. 1962, 24 pages.

* cited by examiner

| Treatment | P. vulnus 15d | P. hanatus 15d | P. vulnus 30d | P. hanatus 30d | P. vulnus 60d | P. hanatus 60d |
|---|---|---|---|---|---|---|
| Garland 2500ppm | 6 | 41 ab | 16.5 | 201 ab | 42.5 | 94.5 a |
| Propionic A 1500ppm | 24 | 91 a | 35 | 174 a | 40 | 184 a |
| HyCyn 750ppm | 0 | 0 b | 0 | 0 b | 0 | 0 b |
| Water only check | 13 | 124 a | 11 | 264 a | 26 | 131 a |
| P=0.05 | ns | | ns | | ns | |

FIG. 2

| Treatment | 15 DAT | 30 DAT | 60 DAT |
|---|---|---|---|
| Garland 2500ppm | 47 ab | 117 ab | 137 a |
| Propionic A 1500ppm | 115 a | 218 a | 223 a |
| HyCyn 750ppm | 0 b | 0 b | 0 b |
| Water only check | 176 a | 121 a | 157 a |
| P=0.05 | | | |

FIG. 3

| Dose in ppm (v/v) | P. vulnus 15day | P. tognatus 15day | P. vulnus 30d | P. tognatus 30d | P. vulnus 60d | P. tognatus 60d |
|---|---|---|---|---|---|---|
| 200 ppm | 84% abc | 69.5% ab | 2.9x abc | 0% abc | 66% ns | 52% ab |
| 300 | 0% a | 67% ab | 1.3x abc | 1.2x a | 56% | 28% a |
| 400 | 78% abc | 88% ab | 49% abc | 1.1x abc | 66% | 86% bc |
| 600 | 97% bc | 100% b | 93% c | 99.3% bc | 100% | 98% c |
| 750 | 100% c | 100% b | 100% c | 100% c | 100% | 100% c |

FIG. 4

| HyCyn & PA rates and combinations | Population Means | DMRT @ 0.05% | DMRT @ 0.01% |
|---|---|---|---|
| 200ppm HyCyn | 198 | ab | ab |
| 300ppm HyCyn | 244 | ab | a |
| 400ppm HyCyn | 126 | abc | abc |
| 600ppm HyCyn | 4 | cd | bc |
| 750ppm HyCyn | 0 | d | c |
| 300ppm PA | 405 | a | a |
| 400ppm PA | 180 | ab | a |
| 300ppm HyCyn + 300ppm PA | 223 | ab | a |
| 400ppm HyCyn + 400ppm PA | 126 | bc | abc |
| Water only | 337 | ab | a |

FIG. 5

| HyCyn & PA rates and combinations | Population Means | Population DMRT @ 0.05% |
|---|---|---|
| 200ppm HyCyn | 15 | ab |
| 300ppm HyCyn | 22 | ab |
| 400ppm HyCyn | 6.5 | abc |
| 600ppm HyCyn | 0.25 | c |
| 750ppm HyCyn | 0 | c |
| 300ppm PA | 45 | ab |
| 400ppm PA | 43.5 | a |
| 300ppm HyCyn+ 300ppm PA | 25 | a |
| 400ppm HyCyn+ 400ppm PA | 5 | bc |
| Water only | 34 | a |

FIG. 6

| myCyn treatment | Rep 1 | Rep 2 | Rep 3 | Rep 4 | mean |
|---|---|---|---|---|---|
| untreated | 39M | 31.25M | 13.5M | 21.25M | 26.25M |
| 500ppm | 118.7M | 63M | 45.75M | 20.25M | 61.92M |
| 750ppm | 49.25M | 34.5M | 33.5M | 25.75M | 35.75M |
| 1000ppm | 52.75M | 96.25M | 19M | 65M | 58.25M |
| 1500ppm | 9.75M | 58M | 36M | 84.25M | 47M |

| HvCyn | Rep 1 | Rep 2 | Rep 3 | Rep 4 | mean |
|---|---|---|---|---|---|
| Water only | 9.75M | 11M | 5.75M | 15.25M | 10.4M |
| 500ppm | 13.75M | 10.75M | 8.75M | 2.25M | 8.9M |
| 750ppm | 3M | 34.75M | 8.75M | 8.75M | 13.8M |
| 1000ppm | 9M | 12.5M | 5.25M | 6.5M | 8.3M |
| 1500ppm | 7.75M | 5M | 4.25M | 18.75M | 8.9M |

| LVGyn treatments | Rep 1 | Rep 2 | Rep 3 | Rep 4 | means | |
|---|---|---|---|---|---|---|
| Untreated | 7,500 | 52,500 | 22,500 | 2,500 | 21,250 | bc |
| 500ppm | 12,500 | 22,500 | 42,500 | 5,750 | 20,812 | bc |
| 750ppm | 2,500 | 25,000 | 2,500 | 1,000 | 7,750 | c |
| 1000ppm | 600,000 | 250,000 | 40,000 | 35,000 | 231,250 | a |
| 1500ppm | 42,500 | 17,500 | 17,500 | 30,000 | 26,875 | ab |

| LvGyn | Rep 1 | Rep 2 | Rep 3 | Rep 4 | mean | |
|---|---|---|---|---|---|---|
| Water only | 2,000 | 25,000 | 27,500 | 15,000 | 17,400 | c |
| 500ppm | 50,000 | 32,500 | 4,250 | 237,500 | 81,062 | abc |
| 750ppm | 3,750 | 100,000 | 22,500 | 10,000 | 34,062 | bc |
| 1,000ppm | 600,000 | 1,050,000 | 72,500 | 75,000 | 449,375 | a |
| 1,500ppm | 30,000 | 775,000 | 250,000 | 52,500 | 395,000 | ab |

| LiveQPCR | Rep 1 | Rep 2 | Rep 3 | Rep 4 | mean | | % incidence |
|---|---|---|---|---|---|---|---|
| All Fusarium spp | | | | | | | |
| Water only ck | 20,000 | 13,333 | 750 | 6,667 | 10,187 | ns | |
| 750ppm | 3,333 | 17,500 | 7,500 | 15,833 | 11,041 | | |
| 1500ppm | 11,667 | 15,000 | 17,500 | 0 | 11,041 | | |
| 3000ppm | 5,000 | 9,167 | 10,000 | 10,833 | 8,750 | | 14% |
| 5000ppm | 1667 | | | | | | |
| F. oxysporum | | | | | | | |
| Water only ck | 6,250 | 667 | 1083 | 1883 | 2471 | a | |
| 750ppm | 167 | 500 | 1167 | 2500 | 1083 | a | 56% |
| 1500ppm | 0 | 0 | 2333 | 0 | 583 | b | 76% |
| 3000ppm | 0 | 0 | 0 | 0 | 0 | b | 100% |
| 5000ppm | 0 | | | | | | |
| | No Verticillium detected in any sample | | | | | | |

FIG. 11

| qPCR | Rep 1 | Rep 2 | Rep 3 | Rep 4 | mean | change |
|---|---|---|---|---|---|---|
| All Fusarium | | | | | | |
| water only/ck | 1,000 | 1,917 | 1,833 | 2,000 | 1,687 b | |
| 750ppm | 1,167 | 333 | 4,917 | 2,583 | 2,250 b | 1.33x |
| 1500ppm | 3,750 | 2,417 | 40,000 | 69,167 | 28,833 a | 17x |
| 3000ppm | 250 | 88 | 167 | 1,250 | 439 b | 74% |
| F. oxysporum | | | | | | |
| water only/ck | 13 | 94 | 0 | 56 | 41 c | |
| 750ppm | 638 | 150 | 583 | 188 | 390 b | 9.5x |
| 1500ppm | 1,600 | 800 | 20,000 | 18,333 | 10,183 a | 248x |
| 3000ppm | 38 | 81 | 75 | 131 | 81 bc | 2x |

No Verticillium detected in any sample

FIG. 12

| AITC conc. | Selection of Sumac Petals (Leaves) | Selection of Sumac Petals (Leaves) | Selection of Sumac Petals (Leaves) | Selection of Nitre Petals | Mean of Petals |
|---|---|---|---|---|---|
| Water only | 0, 0, 0, 0 | 0 | 0, 0, 1, 7, 1 | 0/9 | 0 |
| 750ppm | 0, 0, 0, 0 | 0 | 0, 0, 0, 0 | 0 | 0 |
| 1000ppm | 0, 0, 0, 0 | 0 | 0, 0, 0, 2 | -- | 0 |
| 2000ppm | 0, 1, 1, 0 | 1/2 | 1, 0, 1, 0 | 0/2 | 0.25 |
| 3000ppm | 0, 1, 0, 0 | 0 | 0, 0, 0, 3 | 1/3 | 0.33 |
| 4000ppm | 2, 0, 2, 1 | 1/5 | 0, 0, 1, 0 | 0/1 | 0.17 |

FIG. 13

| HCy, ppm | Rep 1 | Rep 2 | Rep 3 | Rep 4 | Means | % of untreated |
|---|---|---|---|---|---|---|
| 3000ppm | 94 | 31 | 0 | 0 | 31.2 ns | unchanged |
| 4000ppm | 31 | 31 | 31 | 0 | 23.2 | 25% |
| 5000ppm | 63 | 0 | 0 | 0 | 15.8 | 50% |
| 6000ppm | 0 | 0 | 0 | 0 | 0 | 100% |
| untreated | 31 | 0 | 31 | 63 | 31.2 | |
| | | | | | P=0.05 | |

FIG. 14

| HVSynperPA | Rep 1 | Rep 2 | Rep 3 | Rep 4 | Means | | % of untreated |
|---|---|---|---|---|---|---|---|
| 3000ppm | 17 | 17 | 29 | 29 | 23 | b | unchanged |
| 4000ppm | 21 | 25 | 21 | 56 | 31 | b | 134% |
| 5000ppm | 0 | 25 | 21 | 25 | 18 | b | 12% |
| 6000ppm | 0 | 0 | 0 | 4 | 1 | a | 96% |
| untreated | 13 | 22 | 29 | 29 | 23 | b | |
| | | | | | P=0.05 | | |

FIG. 15

| H2O2 ppm | Rep 1 | Rep 2 | Rep 3 | Rep 4 | Means | % of untreated |
|---|---|---|---|---|---|---|
| 3000ppm | 0 | 0 | 188 | 563 | 188 b | 67% |
| 4000ppm | 313 | 0 | 125 | 188 | 156 b | 72% |
| 5000ppm | 188 | 188 | 63 | 125 | 141 b | 75% |
| 6000ppm | 63 | 63 | 63 | 188 | 94 b | 83% |
| untreated | 1000 | 500 | 313 | 438 | 563 a | |
| | | | | | $P=0.05$ | |

FIG. 16

| HVAn bent | Rep 1 | Rep 2 | Rep 3 | Rep 4 | Means | % of untreated |
|---|---|---|---|---|---|---|
| 3000ppm | 111 | 222 | 56 | 0 | 97 b | 65% |
| 4000ppm | 0 | 0 | 0 | 0 | 0 c | 100% |
| 5000ppm | 0 | 56 | 56 | 0 | 28 bc | 90% |
| 6000ppm | 0 | 0 | 0 | 0 | 0 c | 100% |
| untreated | 167 | 333 | 278 | 333 | | |
| | | | | | $P=0.05$ | |

FIG. 17

| H/C ppm | Rep 1 | Rep 2 | Rep 3 | Rep 4 | means | % of untreated |
|---|---|---|---|---|---|---|
| 28DAT | | | | | | |
| 750ppm | 382 | 544 | 168 | 976 | 517 ns | unchanged |
| 1000ppm | 248 | 980 | 62 | 224 | 378 | 27% |
| untreated | 1064 | 113 | 304 | 601 | 520 | |
| 60DAT | | | | | | P=0.05 |
| 750ppm | 310 | 1302 | 12 | 326 | 487 ns | 45% |
| 1000ppm | 66 | 584 | 1678 | 694 | 694 | 21% |
| untreated | 507 | 880 | 1320 | 806 | 878 | |

FIG. 18

| HvGyn ppm | Rep 1 | Rep 2 | Rep 3 | Rep 4 | means | % of untreated |
|---|---|---|---|---|---|---|
| 14DAT | | | | | | |
| 1250ppm | 26 | 4 | 6 | 148 | 46 ns | 94.5% |
| 1500ppm | 0 | 8 | 10 | 0 | 4.5 | 99.5% |
| untreated | 223 | 11 | 321 | 2836 | 848 | |
| 28DAT | | | | | | |
| 1250ppm | 3 | 0 | 0 | 27 | 7.5 ns | 92.6% |
| 1500ppm | 0 | 0 | 6 | 0 | 1.5 | 98.5% |
| untreated | 102 | 25 | 0 | 278 | 101 | |

FIG. 19

| HyCyn ppm | Soil depth | Rep 1 | Rep 2 | Rep 3 | Means | % of untreated |
|---|---|---|---|---|---|---|
| F. oxysporum race- 4 | 0-15cm | | | | | |
| 3000ppm | | 1011 | 339 | 1017 | 789 b | 66% |
| 4500ppm | | 89 | 0 | 356 | 148 b | 94% |
| untreated | | 3056 | 1961 | 2000 | 2339 a | |
| | | | | | P=0.05 | |
| | 15-30cm | | | | | |
| 3000ppm | | 11 | 6 | 0 | 5.6 ns | 98% |
| 4500ppm | | 0 | 139 | 0 | 15.3 | 94% |
| untreated | | 172 | 106 | 494 | 257 | |
| | | | | | P=0.05 | |

FIG. 20

| H/Cd/Bah | Rep 1 | Rep 2 | Rep 3 | Rep 4 | Rep 5 | Rep 6 | means | % of untreated |
|---|---|---|---|---|---|---|---|---|
| 3000ppm | 0 | 42 | 250 | 0 | 83 | 0 | 62.5 b | 74% |
| 4500ppm | 0 | 42 | 0 | 0 | 0 | 0 | 7 b | 97% |
| untreated | 83 | 208 | 333 | 125 | 208 | 458 | 236 a | |
| | | | | | | | P=0.05 | |

FIG. 21

| Soil treatments | rep1 | rep2 | rep3 | rep4 | rep5 | rep6 | rep7 | rep8 | rep8 means |
|---|---|---|---|---|---|---|---|---|---|
| Untreated (g plant biomass) | 40 | 40 | 60 | 20 | 40 | 40 | 60 | 40 | 43 b |
| 1000ppm HyCyn (g plant biomass) | 60 | 60 | 60 | 60 | 60 | 80 | 70 | 80 | 66 a |
| 250ppm 1,3-D EC (g plant biomass) | 20 | 40 | 20 | 40 | 40 | 40 | 20 | 20 | 30 c |
| | | | | | | | | | $P=0.05$ |

FIG. 22

| Jap samples/g | Rep 1 | Rep 2 | Rep 3 | Rep 4 | Means | % of Untreated |
|---|---|---|---|---|---|---|
| In basins | 0 | 0 | 0 | 0 | 0 | 100% |
| Outside of basins | 6.6/g | 2.6/g | 36/g | 15 | 15/g | 86% |
| Untreated | 176/g | 72/g | 68/g | --- | 105/g | |
| Soil samples/250cc | | | | | | |
| In basins | 0 | 0 | 2 | 2 | 1/cc | 99.5% |
| Outside of basins | 224 | 2 | 10 | 2 | 59/cc | 66.5% |
| Untreated | 286 | 224 | 36 | --- | 176/cc | |

FIG. 27

PRE-PLANT BIOCIDE USES OF AQUEOUS CYANAMIDES

CROSS-REFERENCES TO RELATED APPLICATIONS

This application claims the benefit of priority to U.S. Provisional Application No. 62/252,833, filed on Nov. 9, 2015, the contents of which are hereby incorporated in the entirety for all purposes.

BACKGROUND OF THE INVENTION

Various formulations of cyanamide have proven useful to agriculture as a fertilizer. A stable liquid formulation, hydrogen cyanamide (HyCyn), has shown efficacy as a spray to provide uniform bud break. When applied to soil, HyCyn is recognized for its short half-life and reduced dermal and oral toxicity. Alternatively, calcium cyanamide can be applied to soil and produce hydrogen cyanamide in situ. Cyanamide has also been investigated for use as a non-fuming soil treatment against soil pathogens, but results were seldom repeatable. Thus, there remains a need for a highly effective, long-acting, and non-fuming pre-plant biocide for weed, soil pathogen, and pest control. The present invention fulfills this and other needs.

BRIEF SUMMARY OF THE INVENTION

It has now been discovered that an aqueous formulation containing a water-soluble low molecular weight cyanamide or nitrile containing compound, such as hydrogen cyanamide (HyCyn), calcium cyanamide, and the like, can be applied as a pre-plant biocide to a cultivation medium (e.g., soil) for highly effective and long lasting control of weeds, nematodes, fungi, and/or insects, or to eradicate a previously planted crop and prepare the soil for re-planting of the same or a different crop. Compared to soil fumigants, the lack of high affinity for soil particles and high water solubility render these pre-plant biocides as non-fuming. These features provided an attractive alternative to soil fumigants for control of weeds and other pests in agricultural crops due to the increased regulatory burden associated with the use of such volatile and toxic compounds. See, e.g., U.S. Pat. Nos. 7,572,460; 7,968,108; 8,021,648; 8,052,985; and 8,197,834.

In a first aspect, the present invention provides a method for growing a plant using a pre-plant biocide, the method comprising: i) irrigating a cultivation medium; and ii) contacting the cultivation medium with the pre-plant biocide comprising water and a water-soluble low molecular weight cyanamide or nitrile containing compound (e.g., hydrogen cyanamide) at a concentration of 400-10,000 ppm (e.g., 600-10,000 ppm, 600-2,000 ppm, 600-1,000 ppm, or 1,000-2,000 ppm), thereby applying the pre-plant biocide. The pre-plant biocide can be contacted with the cultivation medium before planting a plant into the cultivation medium. The pre-plant biocide can be contacted with the cultivation medium after final harvest and before re-planting. The pre-plant biocide can be contacted with the cultivation medium at least 30-90 days before planting or re-planting.

In some embodiments, the method comprises i) irrigating the cultivation medium to a greater than 50% water saturation level; ii) after the irrigating, allowing the irrigated cultivation medium to drain to a saturation level of 50%-25%; iii) contacting the cultivation medium with the pre-plant biocide comprising water and a water-soluble low molecular weight cyanamide or nitrile containing compound (e.g., hydrogen cyanamide) at a concentration of 400-10,000 ppm, thereby applying the pre-plant biocide; iv) waiting from 30-90 days after the contacting; and v) after the waiting, planting the plant into the cultivation medium, wherein: (a) the applying the pre-plant biocide reduces a number of viable pathogenic nematodes in the root zone of the cultivation medium by at least about 90% (e.g., at least about 93%) at the time of planting relative to an untreated control cultivation medium; (b) the applying the pre-plant biocide reduces a number of viable weeds in the cultivation medium by at least about 90%, 95%, or 99% at the time of planting relative to an untreated control cultivation medium; (c) the applying the pre-plant biocide reduces a number of viable pathogenic fungal organisms in the cultivation medium by at least about 50-90% (e.g., at least about 90%) at the time of planting relative to an untreated control cultivation medium; (d) the applying the pre-plant biocide reduces a number of viable pre-plant tree or vine roots by at least about 50-90% (e.g., at least about 90%) at the time of planting relative to an untreated control cultivation medium, thereby reducing a root rejection component of a re-plant problem; or (e) the applying the pre-plant biocide reduces a number of endoparasitic or ectoparasitic nematodes associated with viable pre-plant tree or vine roots by at least about 50-90% (e.g., at least about 90%) at the time of planting relative to an untreated control cultivation medium, thereby reducing a soil pest component of a re-plant problem.

In some cases, (a) the applying the pre-plant biocide reduces the number of viable pathogenic nematodes in the root zone of the cultivation medium by at least about 90% (e.g., at least about 93%) to a depth of from about 1 to about 5 feet (e.g., 4 feet) at the time of planting a perennial plant relative to an untreated control cultivation medium. In some cases, (a) the applying the pre-plant biocide reduces the number of viable pathogenic nematodes in the root zone of the cultivation medium by at least about 90% (e.g., at least about 93%) to a depth of 2-24 inches (e.g., 2-12, 2-6 or 3-4 inches) at the time of planting an annual plant relative to an untreated control cultivation medium In some cases, (a) the applying the pre-plant biocide reduces a number of viable pathogenic nematodes in the root zone of the cultivation medium by at least about 90% (e.g., at least about 93%) to a depth of from about 1 to about 5 feet (e.g., 4 feet) at the time of planting relative to an untreated control cultivation medium; and (b) the applying the pre-plant biocide reduces a number of viable weeds in the cultivation medium by at least about 50-99% (e.g., at least about 90%, 95%, or 99%) at the time of planting relative to an untreated control cultivation medium. In some cases, (a) the applying the pre-plant biocide reduces a number of viable pathogenic nematodes in the root zone of the cultivation medium by at least about 90-99% (e.g., at least about 93%) to a depth of from about 1 to about 5 feet (e.g., 4 feet) at the time of planting relative to an untreated control cultivation medium; (b) the applying the pre-plant biocide reduces a number of viable weeds in the cultivation medium by at least about 50-99% (e.g., at least about 90%, 95%, or 99%) at the time of planting relative to an untreated control cultivation medium; and (c) the applying the pre-plant biocide reduces a number of viable pathogenic fungal organisms in the cultivation medium by at least about 50 to 99% (e.g., at least about 50%) at the time of planting relative to an untreated control cultivation medium.

In some cases, the contacting comprises drenching the cultivation medium to a depth of 1-10 inches, 2-100 inches, 2-60 inches, or 2-25 inches. In some cases, the contacting comprises drenching the cultivation medium to a depth of 3 inches. In some cases, the contacting comprises drenching the cultivation medium to a depth of 6 inches or 8 inches. In some cases, the pre-plant biocide is applied to target fungi or weed seeds and the contacting comprises drenching the cultivation medium to a depth of 2-4 inches, thereby reducing a number of viable fungi or weed seeds in the cultivation medium by at least about 50-90% relative to an untreated control cultivation medium. In some cases, the pre-plant biocide is applied to protect a perennial crop against nematodes, root rejection or old root systems (e.g., pre-plant tree or vine roots), and the contacting comprises drenching the cultivation medium to a depth of 6-60 inches, thereby reducing a number of viable nematodes, or pre-plant tree or vine roots, in the cultivation medium by at least about 50-90% relative to an untreated control cultivation medium. In some cases, prior to the contacting, the cultivation medium is tilled to a specified tilling depth, and the contacting comprises drenching the cultivation medium to the tilling depth.

In some cases, the pathogenic nematodes comprise endoparasitic nematodes. In some cases, the pathogenic nematodes comprise ectoparasitic nematodes. In some cases, the pathogenic nematodes are at an egg, cyst, or juvenile life cycle stage. In some cases, the pathogenic nematodes are in a dauer larva life cycle stage. In some cases, the pathogenic nematodes comprise pathogenic nematodes of the genus *Helicotylenchus, Hoplolaimus, Meloidogyne, Paratrichodorus, Pratylenchus*, or *Rotylenchulus*. In some cases, the pathogenic nematodes comprise *Meloidogyne* spp *Pratylenchus vulnus, Paratylenchus hamatus, Rotylenchulus reniformis*, or *M. xenoplax*.

In some cases, the pathogenic fungi comprise *Sclerotinia minor, Sclerotinia major, Fusarium* spp *Verticillium dahliae*, or pathogenic fungi from a genus *Trichoderma* or a genus *Fusarium*. In some cases, the weeds comprise *Capsella bursa-pastoris, Solanum sarrachoides, Sonchus* spp., *Portulaca oleraceae, Amaranthus* spp., *Chenopodium album, Malva* spp., *Cyperus rotundus, Cyperus esculentus, Ipomoea hederacea, Ipomoea lacunosa, Senna obtusifolia, Digitaria sanguinalis*, or *Eleusine indica*, or a combination thereof.

In some cases, the applying the pre-plant biocide reduces a number of viable pathogenic nematodes in the root zone of the cultivation medium by at least about 90-99.9% (e.g., at least about 93%) to a depth of from about 1 to about 5 feet (e.g., 4 feet) for 30-365 days (e.g., 30-60 days) after planting relative to an untreated control cultivation medium. In some cases, the applying the pre-plant biocide reduces a number of viable pathogenic nematodes in the root zone of the cultivation medium by at least about 90-99.9% (e.g., at least about 93%) to a depth of from about 1 to about 5 feet (e.g., 4 feet) for more than 30-365 days (e.g., more than 60 days) after planting relative to an untreated control cultivation medium. In some cases, the applying the pre-plant biocide reduces a number of viable pathogenic nematodes in the root zone of the cultivation medium by at least about 90-99.9% (e.g., at least about 93%) to a depth of from about 1 to about 5 feet (e.g., 4 feet) for greater than 1 year after planting relative to an untreated control cultivation medium.

In some cases, the pre-plant biocide comprises water and hydrogen cyanamide. In some cases, the pre-plant biocide comprising water and hydrogen cyanamide is a soil or plant metabolizable biocide solution. In some cases, the soil metabolizable biocide solution comprises hydrogen cyanamide, in an amount of from about 0.1% to about 20% (w/v); a polyhydroxy organic compound soluble in water, in an amount of from about 10% to about 90% (w/w); and water to 100%. In some cases, the polyhydroxy compound is selected from the group consisting of glycerin, a sugar alcohol, ethylene glycol, propylene glycol, erythritol, xylitol, and mannitol. In some cases, the applying the pre-plant biocide (e.g., comprising water and hydrogen cyanamide) provides at least a one-year supply of available nitrogen to the plant. In some cases, the applying the pre-plant biocide (e.g., comprising water and hydrogen cyanamide) provides a greater than one-year supply of available nitrogen to the plant.

In some cases, the plant is a perennial plant. In some cases, the plant is an annual plant. In some cases, the plant is of the genus *Vitis, Fragaria, Juglans, Malus, Citrus, Pistacia*, or *Prunus*. In some cases, the applying the pre-plant biocide provides a 10% to a 600% (e.g., 110% to 600%) improved first year growth benefit relative to a control plant planted in an untreated control cultivation medium.

BRIEF DESCRIPTION OF THE DRAWINGS

FIG. 2: illustrates results from a comparison of three nematicidal agents on various indicated nematode populations at 15, 30, and 60 days after treatment. HyCyn at 750 ppm demonstrates elimination of endo and ecotparasitic nematodes in test soil screened free of roots at all times tested. Results are binned using Duncan's Multiple Range Test (DMRT).

FIG. 3: illustrates results from a comparison of three nematicidal agents on combined populations of *P. vulnus* and *P. hamatus* 15, 30, and 60 days after treatment (DAT). Results are binned using Duncan's Multiple Range Test (DMRT).

FIG. 4: illustrates results of a dose response analysis of the nematicidal activity of HyCyn on *P. vulnus* and *P. hamatus* 15, 30, and 60 days after treatment. Results are binned using Duncan's Multiple Range Test (DMRT).

FIG. 5: illustrates results of application of the indicated concentrations of HyCyn with or without proprionic acid (PA) on the mean population of endoparasitic and ectoparasitic nematodes one month after treatment. Population means are calculated from 8 replicate experiments. Results are binned using Duncan's Multiple Range Test (DMRT) at $p=0.05$ and $p=0.01$.

FIG. 6: illustrates results of application of the indicated concentrations of HyCyn with or without proprionic acid (PA) on the mean population of endoparasitic and ectoparasitic nematodes sixty days after treatment. Population means are calculated from 4 replicate experiments. Results are binned using Duncan's Multiple Range Test (DMRT) at $p=0.05$.

FIG. 7: illustrates results of HyCyn treatment of soil on total soil bacteria populations (cfu/g) 14 days after treatment.

FIG. 8: illustrates results of HyCyn treatment of soil on total soil bacteria populations (cfu/g) 28 days after treatment.

FIG. 9: illustrates results of HyCyn treatment of soil on total soil yeast populations (cfu/g) 14 days after treatment.

FIG. 10: illustrates results of HyCyn treatment of soil on total soil yeast populations (cfu/g) 28 days after treatment.

FIG. 11: illustrates results of HyCyn treatment of soil on total *Fusarium* spp./g 14 days after treatment.

FIG. 12: illustrates results at a second field location of HyCyn treatment of soil on total *Fusarium* spp./g 14 days after treatment.

FIG. 13: illustrates results of HyCyn treatment of soil on total *Sclerotinia* spp./g 14 days after treatment.

FIG. 14: illustrates results of HyCyn treatment of silt soil from a strawberry field near Santa Maria, Calif., drenched with 3,000; 4,000; 5,000; or 6,000 ppm HyCyn solutions or water to determine application rates to control *Fusarium oxysporum*. Soil was sampled at 30 DAT, and data are reported as propagules per gram.

FIG. 15: illustrates results of HyCyn treatment of silt soil from a strawberry field near Santa Maria, Calif., drenched with 3,000; 4,000; 5,000; or 6,000 ppm HyCyn solutions or water to determine application rates to control *Fusarium oxysporum*. Soil was sampled at 70 DAT, and data are reported as propagules per gram.

FIG. 16: illustrates results of HyCyn treatment of silt soil from a strawberry field near Santa Maria, Calif., drenched with 3,000; 4,000; 5,000; or 6,000 ppm HyCyn solutions or water to determine application rates to control *Cylindrocarpon* spp. Soil was sampled at 30 DAT, and data are reported as propagules per gram.

FIG. 17: illustrates results of HyCyn treatment of silt soil from a strawberry field near Santa Maria, Calif., drenched with 3,000; 4,000; 5,000; or 6,000 ppm HyCyn solutions or water to determine application rates to control *Cylindrocarpon* spp. Soil was sampled at 70 DAT, and data are reported as propagules per gram.

FIG. 18: illustrates results of HyCyn treatment in Wasco sandy loam, 28 DAT and 60 DAT on *Meloidogyne incognita* populations for carrots drenched at 10° C.

FIG. 19: illustrates results of HyCyn treatment in Wasco sandy loam, 14 DAT and 28 DAT on *Meloidogyne incognita* populations for sweet potato crops drenched at 15° C.

FIG. 20: illustrates results of HyCyn treatment in sandy loam soil at 10° C. on *F. oxysporum* race-4 populations 28 DAT. Soil was collected at the indicated depth.

FIG. 21: illustrates results of HyCyn treatment in sandy loam soil at 10° C. on *F. oxysporum* race-4 populations 70 DAT. Soil was collected at 0-20 cm.

FIG. 22: illustrates improved growth of trees cultivated for two months in soil treated with a HyCyn containing pre-plant biocide.

FIG. 27: illustrates eradication of *P. vulnus* from roots and soil within basins treated to 4 ft deep at 30 DAT.

DETAILED DESCRIPTION OF THE INVENTION

I. General

Figure 1:
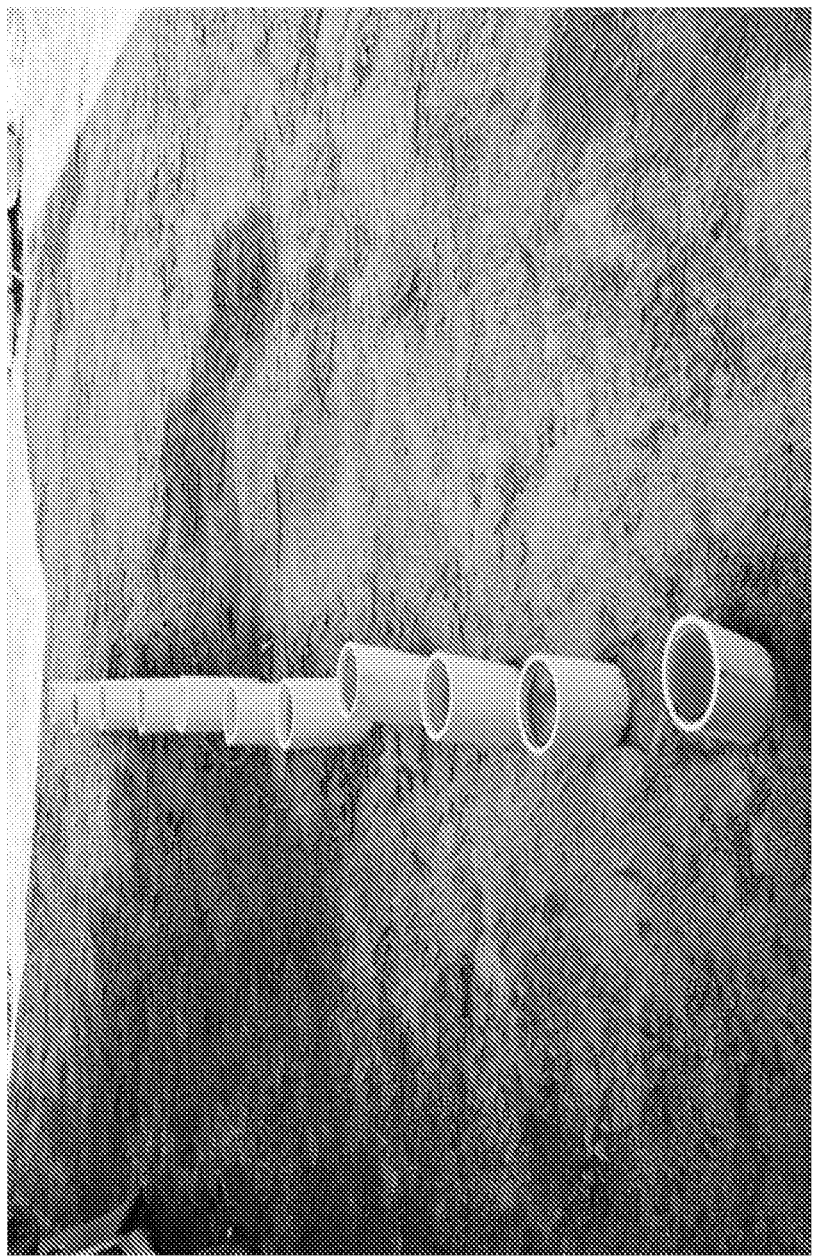
FIG. 1: illustrates a system for assessing biocide activity. Soil columns 3 inches in diameter and 30 inches in length are filled with 22 inches of tamped soil and drenched with various products with and without adjuvants.

Methods and compositions are provided for use of a stable aqueous formulation of a water-soluble low molecular weight cyanamide or nitrile containing compound as a pre-plant biocide. The methods and compositions described herein are particularly concerned with controlling the growth or organisms such as insects, fungi, nematodes, and/or weeds that are deleterious to crop growth. The methods and compositions described herein are an attractive alternative to the use of fumigants or other environmentally burdensome biocides. Components of this biocide can comprise 1 part carbon and 2 parts nitrogen, wherein the carbon and nitrogen are double- or triple-bonded to each other. Components of the biocide can further comprise hydrogen and a buffer, such as a phosphate buffer. Without wishing to be bound by theory, cleavage of associated double or triple carbon:nitrogen bonds on the surface or within organisms provides the suspected mode of action. HyCyn is of lower toxicity compared to similar nitrogen-carbon compounds having double or triple carbon:nitrogen bonds. However, other nitrogenous compounds of similar molecular weight that are systemic, biocidal, and highly water soluble can exhibit similar pre-plant biocidal activity.

II. Definitions

The term "water-soluble low molecular weight cyanamide or nitrile containing compound" refers to a compound containing at least one C=N or C≡N group, having a molecular weight of between 27 and 100 g/mol, and a solubility in water of at least 400 mg/L.

The term "hydrogen cyanamide," "HyCyn," and the like, is used herein to denote a compound of the formula

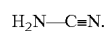

$H_2N-C\equiv N$.

This compound is also referred to among chemists as cyanamide, cyanogenamide, and carbodiimide, and is to be distinguished from the calcium salt, calcium cyanamide

$[Ca^{2+}][^-N=C=N^-]$.

The term "ethanedinitrile" refers to a compound of the formula

$N\equiv C-C\equiv N$.

The term "ppm," unless otherwise indicated, refers to mg of a water-soluble low molecular weight cyanamide or nitrile containing compound, such as HyCyn, per liter of liquid (e.g., water). One of skill in the art will appreciate that a formulation of pre-plant biocide at a specified concentration of active ingredient (e.g., HyCyn) can be provided by mixing a specified volume of water, optionally containing stabilizers, wetting agents, detergents, pH modifiers, salts, other biocidal or fertilizing agents and the like, with a specified volume of a concentrated stock solution of the active ingredient. As an example, a 1000 ppm pre-plant biocide can be formulated by mixing 1000 gallons of water with 2 gallons of a stock solution containing 50% by weight HyCyn, such as found in the commercially available DORMEX® or L500® products.

"Cultivation medium" refers to a medium in which plants can grow. The cultivation medium can be, e.g., greenhouse potting media, or soil. Soil can comprise decaying organic matter, humus, clay, sand, silt, stones, animal waste products, and water, for example. The types of soils in which the methods and compositions of this invention can be effective are sandy soils, loamy soils, clays, silt, and combinations such as sandy loam, silty loam, sandy clay, and the like. As is known in the art, soil can vary as a function of depth from the surface, topography, and location, among other factors. In some embodiments, the cultivation medium is well-tilled soil.

"Irrigating" in the context of irrigation of a cultivation medium in preparation for contacting with a pre-plant biocide refers to contacting the cultivation medium with a sufficient quantity of water over a sufficient quantity of time to achieve a specified level of water saturation. Irrigation can be performed by any method known in the art for delivering water to a cultivation medium. For example, the irrigation can be performed with sprinklers (e.g., non-misting sprinklers), a drip irrigation system, by soil drenching (e.g., into basins), and the like.

"% water saturation level" refers to an amount of water saturation of a cultivation medium (e.g., soil). At saturation, all soil pore space is occupied by water and no free water collects on the soil surface. Thus, at 50% water saturation level, e.g., half of the soil pore space is occupied by water. % water saturation can be measured by methods known in the art. See, e.g., Wilcox, Soil Science, September 1951, Volume 72, Issue 3, p. 233-38.

The term "soil drench" refers to applying a relatively large volume of a liquid to a soil, and is distinguished from spraying or misting.

The term "pre-plant biocide" refers to a formulation (e.g., aqueous formulation) containing a water-soluble low molecular weight cyanamide or nitrile containing compound (e.g., hydrogen cyanamide) in sufficient concentration to exhibit biocidal activity against one or more target organisms (e.g., nematodes, weeds, previously planted crops, etc.).

"Contacting the cultivation medium with the pre-plant biocide," and "applying the pre-plant biocide" refers to any suitable method for delivering a pre-plant biocide to a cultivation medium in sufficient quantity. In some embodiments, the pre-plant biocide is delivered via drench irrigation. In certain embodiments, delivery of the pre-plant biocide is performed under conditions suitable to provide a sufficient quantity with uniformity (e.g., throughout a zone of planting) to a specified depth (e.g., 6-8 inches, 2-4 inches, 2-60 inches, 1-10 inches, 4-60 inches, or 6-60 inches) of the cultivation medium.

"Planting the plant into the cultivation medium" refers to any method known in the art to bring a plant (e.g., seed, rooting, seedling, etc.) into contact with a cultivation medium (e.g., soil) under conditions that promote growth of the plant.

"Weed" refers to a plant whose growth in an agricultural context is not desired. A weed growing at the same time and place as a crop plant can compete with the crop for resources, such as nutrients, water, or sunlight, and hinder or reduce the growth of the crop. Accordingly, the growth of weeds may be controlled (see definition of 'controlling organism growth'). Representative weeds include, but are not limited to, yellow nutsedge, crabgrass, teaweed, sicklepod, and morning glory.

Reducing "a number of viable weeds in the cultivation medium" refers to killing weeds (e.g., plants or seeds) or otherwise rendering the weeds incapable of growing in the cultivation medium by applying the pre-plant biocide. The level of reduction can be determined relative to a control untreated cultivation medium by, e.g., allowing the test and control media to grow any resident viable weeds. The difference in the number of weeds detected after a suitable assay period (e.g., 1, 2, 3, 4, 5, 6, 7, 8, 9, or 10 weeks after application of biocide) can then be used to determine the level of reduction produced by the pre-plant biocide.

"Nematode" refers to a roundworm (e.g., true roundworm) belonging to the phylum Nematoda or Nemathelminthes. Nematodes can be pathogenic or beneficial. Exemplary nematodes include, but are not limited to pathogenic nematodes of the genus *Helicotylenchus, Hoplolaimus, Meloidogyne, Paratrichodorus, Pratylenchus* (e.g., *P. vulnus*), *Paratylenchus* (e.g., *P. hamatus*), *Radopholus*, or *Rotylenchulus* (e.g., *R. reniformis*).

Reducing "a number of viable pathogenic nematodes in the root zone of the cultivation medium" refers to killing pathogenic nematodes or otherwise rendering the pathogenic nematodes incapable of harming (e.g., reducing growth rate and/or productivity of) the plant by applying the pre-plant biocide to the root zone of the cultivation medium. The "root zone" refers to the zone of cultivation medium in which the roots of the plant are established. Thus, the "root zone" is dependent on the plant, the age of the plant, and its manner of cultivation. The level of reduction can be determined relative to a control untreated cultivation medium by, e.g., sampling the root zone of treated and untreated cultivation medium after a suitable period of time (e.g., 1, 2, 3, 4, 5, 6, 7, 8, 9, or 10 weeks after application of biocide) and assaying (e.g., via culture or polymerase chain reaction) the media to quantitate a number of pathogenic nematodes. The difference in the number of pathogenic nematodes can then be used to determine the level of reduction produced by the pre-plant biocide.

"Fungus" refers to any organism belonging to the kingdom Fungi. The fungus can be pathogenic or deleterious. Representative fungi include, but are not limited to, *Sclerotinia minor, Sclerotinia major, Fusarium* spp., *Verticillium dahliae*, or other pathogenic fungi from the genera *Trichoderma* or *Fusarium*.

Reducing "a number of viable pathogenic fungal organisms in the cultivation medium" refers to killing pathogenic fungi or otherwise rendering the pathogenic fungi incapable of harming (e.g., reducing growth rate and/or productivity of) the plant by applying the pre-plant biocide to the cultivation medium. The level of reduction can be determined relative to a control untreated cultivation medium by, e.g., sampling the treated and untreated cultivation medium after a suitable period of time (e.g., 1, 2, 3, 4, 5, 6, 7, 8, 9, or 10 weeks after application of biocide) and assaying (e.g., via culture or polymerase chain reaction) the media to quantitate a number of pathogenic fungal organisms. The difference in the number of pathogenic fungi can then be used to determine the level of reduction produced by the pre-plant biocide.

"Soil metabolizable biocide solution" refers to a solution containing an active biocide agent (e.g., HyCyn) that rapidly breaks down or is rapidly metabolized by one or more resident soil organisms into a non-toxic and/or beneficial product. For example, compositions containing HyCyn that break down within 15-90 days after application to soil into carbon dioxide, and urea or ammoniacal forms of nitrogen are "soil or plant metabolizable."

"Polyhydroxy organic compounds" refers to organic compounds having multiple hydroxyl groups. The polyhydroxy organic compounds can have 2, 3, 4, 5, 6 or more hydroxy groups. Moreover, the polyhydroxy organic compound can have any suitable molecular weight, but is typically less than 1000 g/mol, or less than 500 g/mol, or less than 250 g/mol.

Representative compounds include, but are not limited to, glycerin (also called glycerine and glycerol), ethylene glycol, propylene glycol, erythritol, xylitol, mannitol, other sugar alcohols, and various sugars (e.g. glucose and fructose).

"First year growth benefit" refers to an increase in growth of a plant in the first year after planting the plant into cultivation medium that has been treated with a pre-plant biocide as compared to a control plant that is planted into control medium that is not treated with the pre-plant biocide. The level of growth benefit can be assayed by measuring a change in plant height, mass, diameter, or yield.

III. Compositions

Hydrogen cyanamide can be obtained commercially, for example as a purified solid or as the liquid composition DORMEX® or L500® (50%> hydrogen cyanamide by weight, sold by AlzChem AG, Trostberg, Germany). Alternatively, hydrogen cyanamide can be prepared from dissolution or hydrolysis of calcium cyanamide, which is commercially available from AlzChem, Sigma-Aldrich (St. Louis, Mo.), and other vendors. Hydrogen cyanamide can serve as a fertilizer for some crops, and can also act as a pesticide or herbicide, suppressing the growth of unwanted organisms such as weeds, insects, fungi, or nematodes that may compete with crops for resources. Other water-soluble low molecular weight cyanamide or nitrile containing compounds can also be obtained commercially.

A water-soluble low molecular weight cyanamide or nitrile containing compound (e.g., hydrogen cyanamide) can be present in a pre-plant biocide in any suitable amount, such as from about 0.01% to about 50% (w/v) or from about 0.04% to about 20% (w/v). The compound (e.g., hydrogen cyanamide) can be present in the pre-plant biocide in an amount of from about 0.05% to about 10% (w/v), or from about 0.1% to about 10% (w/v), or from about 0.5% to about 5% (w/v), from about 0.5% to about 1% (w/v), from about 0.01% to about 1%, from about 0.01% to about 0.5%, from about 0.04% to about 1%, from about 0.04% to about 0.5%, from about 0.06% to about 1%, or from about 0.06% to about 0.5%. The compound (e.g., hydrogen cyanamide) can be present in the pre-plant biocide in an amount of about, or at least about, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1% (w/v). In some embodiments, the compound (e.g., hydrogen cyanamide) is present in a composition applied to a cultivation medium as a pre-plant biocide in an amount of about, or at least about, 200 ppm; 300 ppm; 400 ppm; 500 ppm; 600 ppm; 700 ppm; 800 ppm; 900 ppm; 1,000 ppm; 1,500 ppm; 2,000 ppm; 3,000 ppm; 4,000 ppm; 5,000 ppm; 6,000 ppm; 7,000 ppm; 8,000 ppm; 9,000 ppm; 10,000 ppm; 12,000 ppm; 15,000 ppm; or 20,000 ppm. In some embodiments, the compound (e.g., hydrogen cyanamide) is present in a composition applied to a cultivation medium as a pre-plant biocide in an amount of from about 200 ppm to about 2,000; 5,000; or 10,000 ppm; from about 400 ppm to about 2,000; 5,000; or 10,000 ppm; from about 600 ppm to about 2,000; 5,000; or 10,000 ppm; or from about 1,000 ppm to about 2,000; 5,000; or 10,000 ppm.

As described herein, the water-soluble low molecular weight cyanamide or nitrile containing compound has a solubility in water of at least 400 mg/L. In some cases, the compound has a solubility in water of at least 500, 600, 700, 800, or 900 mg/L. In some cases, the compound has a solubility in water of, of at least, of about, or of at least about, 1, 2, 3, 4, 5, 6, 7, 8, 9, 10, 11, 12, 13, 14, 15, 16, 17, 18, 19, 20, 25, 30, or 40 g/L. In some cases, the compound has a solubility in water of from about 5 g/L to about 200 g/L, from about 5 g/L to about 100 g/L, from about 10 g/L to about 200 g/L, from about 10 g/L to about 100 g/L, from about 10 g/L to about 90 g/L, from about 20 g/L to about 200 g/L, from about 20 g/L to about 100 g/L, from about 20 g/L to about 90 g/L, from about 30 g/L to about 200 g/L, from about 30 g/L to about 100 g/L, or from about 30 g/L to about 90 g/L.

Polyhydroxy organic compounds useful in the compositions of the present invention can be straight-chain alkanes or cycloalkanes substituted with two or more hydroxyl groups, and are generally soluble in water. Representative polyhydroxy organic compounds include, but are not limited to, sugars, sugar alcohols, ethylene glycol, glycerol, glycerin, propylene glycol, erythritol, threitol, arabitol, ribitol, xylitol, mannitol, sorbitol, galactitol and iditol. In some embodiments, the polyhydroxy organic compound can be glycerin, ethylene glycol, propylene glycol, erythritol, xylitol, or mannitol. In other embodiments, the polyhydroxy organic compound can be glycerin. In some other embodiments, the polyhydroxy organic compound can be bioglycerin. Without being bound by any theory, the polyhydroxy compound can serve as a metabolizable carbon source for organisms to which the composition is applied.

The polyhydroxy organic compounds can be obtained by any suitable means, such as from commercial sources, from synthetic sources, or as by-products of other processes. For example, glycerin can be obtained from the production of a number of processes, including the production of biodiesel fuel. For example, approximately 100 kg of glycerin can be produced per 1000 kg biodiesel. Glycerin obtained along with biodiesel is termed 'bioglycerin', and in some embodiments the polyhydroxy organic compound is bioglycerin.

The polyhydroxy organic compound can be present in any suitable amount in the pre-plant biocide composition of the present invention, such as from about 10% to about 90%> (w/w). The polyhydroxy organic compound can also be present in an amount of from about 25% to about 75%) (w/w), or from about 35% to about 65%, or from about 45% to about 60%>, or from about 50%) to about 60%> (w/w). The polyhydroxy organic compound can also be present in the composition in an amount of about 50%>, 51, 52, 53, 54, 55, 56, 57, 58, 59 or 60%> (w/w). In some embodiments, the polyhydroxy organic compound can be present in an amount of about 54% (w/w).

The pre-plant biocide of the present invention can also include any suitable organic acid. Representative organic acids include $C_{1-6}$ alkanoic acid, i.e., a straight-chain carboxylic acid having between one and six carbon atoms, the corresponding partially saturated alkanoic acids, and aromatic organic acids. Examples of $C_{1-6}$ alkanoic acids include, but are not limited to, monocarboxylic acids (e.g., formic acid, acetic acid, proprionic acid, or butyric acid), and dicarboxylic acids (e.g., malonic acid, or succinic acid). Alkanoic acids are available from many commercial sources. In some embodiments, the composition also includes a $C_{1-6}$ alkanoic acid. In some embodiments, the alkanoic acid can be formic acid, acetic acid, propionic acid, malonic acid, butyric acid or succinic acid. In some other embodiments, the alkanoic acid can be formic acid, acetic acid, propionic acid or butyric acid. In still other embodiments, the alkanoic acid can be propionic acid.

When the composition includes an alkanoic acid, any suitable of alkanoic acid can be used in the composition. For example, the alkanoic acid can be present in an amount of from about 1% to about 25% (w/w), or from about 5 to about 15% (w/w), or from about 6%> to about 12% (w/w). The alkanoic acid can also be present in the composition in an amount of about 5%>, 6, 7, 8, 9, 10, 11, 12, 13, 14 or 15% (w/w). The alkanoic acid can also be present in the composition in an amount of about 8.0%>, 8.1, 8.2, 8.3, 8.4, 8.5, 8.6, 8.7, 8.8, 8.9 or 9.0%) (w/w). Without being bound by any theory, the alkanoic acids can stabilize the cyanamide composition, slowing the decomposition of hydrogen cyanamide (see e.g. U.S. Pat. No. 7,572,460; and International Patent Application Publication No. WO/2014/169,175, incorporated herein in the entirety).

The pre-plant biocide composition of the present invention can also include any suitable base. For example, the base can be a strong base such as sodium hydroxide (NaOH) or potassium hydroxide (KOH). In some embodiments, the composition can also include a strong base. In other embodiments, the strong base can be NaOH or KOH. In some other embodiments, the strong base can be KOH.

When a base is present in the pre-plant biocide composition of the present invention, any amount of base can be suitable. For example, the base can be present in an amount of from about 1% to about 25%) (w/w) of the base, or from about 1% to about 10%>, or from about 1% to about 5% (w/w). The base can also be present in the composition in an amount of about 1%, 2, 3, 4, 5, 6, 7, 8, 9 or 10% (w/w). In some embodiments, the base can be present in an amount of about 3%) (w/w). The base can be present as a concentrated solution of base in water, or a more dilute solution. For example, the base can be present as a 25%, 35, 45, 50, 55, 65 or 75% base in water solution. In some embodiments, the base can be present in an amount of from about 7% (w/w), as a 45% potassium hydroxide solution.

The pre-plant biocide composition of the present invention can also include an acid such as a mineral acid. Mineral acids useful in the compositions of the present invention include, but are not limited to, hydrochloric acid, nitric acid, phosphoric acid, sulfuric acid, boric acid, or perchloric acid. In some embodiments, the pre-plant biocide composition of the present invention includes an acid. In other embodiments, the pre-plant biocide composition includes a mineral acid. In some other embodiments, the pre-plant biocide composition includes a mineral acid that can be hydrochloric acid, nitric acid, phosphoric acid, sulfuric acid, boric acid, or perchloric acid. In yet other embodiments, the mineral acid can be phosphoric acid.

The mineral acid can be present in the composition in any suitable amount. For example, the mineral acid can be present in an amount of from about 0.1% to about 10% (w/w), or from about 0.1% to about 5% (w/w), or from about 1% to about 5% (w/w). The mineral acid can also be present in an amount of about 1.0%, 1.25, 1.5, 1.75, 2.0, 2.25, 2.5, 2.75, 3.0, 3.25, 3.5, 3.75, 4.0, 4.25, 4.5, 4.75 or 5.0% (w/w). The mineral acid can be a concentrated solution, or a more dilute solution. For example, concentrated phosphoric acid can be 85% phosphoric acid in water (w/w). Other concentrations are useful, such as 50%, 55, 60, 65, 70, 75, 80 or 85% phosphoric acid in water (w/w). In some embodiments, the phosphoric acid can be present in the composition in an amount of about 3% (w/w), as a 75% phosphoric acid solution.

The pre-plant biocide composition of the present invention can have any suitable pH. For example, the composition can be from about 4 to about 10, or from about 4 to about 7, or from about 5 to about 7. The pH of the composition can also be less than about 5, 6 or 7. The pH of the composition can also about 5, 6 or 7. In some embodiments, the composition can have a pH of less than about 6. In other embodiments, the pH can be about 5. In some embodiments, the composition can have a pH of less than or less than about 5. In some embodiments, the pH can be about 4.5. In some embodiments, the pH can be from about 3.5 to about 4.5. In some embodiments, the pH can be from about 4.0 to about 4.3 or 4.5. The pH can be maintained at a particular value by any means in the art. For example, the composition can include any suitable buffer.

In some embodiments, the present invention provides a pre-plant biocide composition including hydrogen cyanamide, in an amount of about 6% (w/w), glycerin, in an amount of about 54% (w/w), propionic acid, in an amount of about 8.6% (w/w), a 45% potassium hydroxide solution, in an amount of about 7% (w/w), a 75% phosphoric acid solution, in an amount of about 3% (w/w), and water to 100%.

The pre-plant biocide composition can also include urea in any suitable amount. For example, urea can be present in an amount of from about 1% to about 15% (w/w), or from about 1% to about 10%) (w/w), or from about 1% to about 5% (w/w), or from about 5% to about 10% (w/w). The urea can also be present in an amount of about 1%, 1.5, 2.0, 2.5, 3.0, 3.5, 4.0, 4.5, 5.0, 5.5, 6.0, 6.5, 7.0, 7.5, 8.0, 8.5, 9.0, 9.5 or about 10% (w/w). In some embodiments, the urea can be present in an amount of about 6.8% (w/w). In other embodiments, the urea can be present in an amount of about 3.4% (w/w).

The pre-plant biocide compositions of the present invention can include other components, such as fertilizers, pesticides (herbicides, insecticides, or fungicides, or combinations thereof), additives, diluents, stabilizers, colorants, buffers, plant growth regulators, defoliants, etc. Examples of such adjuvants are formulating aids, buffers and other stabilizers, solubilizing agents, and dispersing agents. These materials are well known in the agricultural formulations industry and readily available from suppliers of agricultural chemicals. Any of these additional substances can be included in the compositions of the present invention.

III. Methods

The present invention provides methods of controlling the growth of unwanted and undesirable organisms in soil, using a pre-plant biocide of the present invention (e.g., an aqueous formulation of hydrogen cyanamide or other water-soluble low molecular weight cyanamide or nitrile containing compound). In some embodiments, the present invention provides a method of controlling organism growth, including contacting soil with a pre-plant biocide composition of the present invention, in an amount effective to control the growth of the organism. In some embodiments, the present invention provides a method of cultivating a plant in a cultivation medium that has been prepared with a pre-plant biocide as described herein in an amount effective to control the growth of the organism, wherein the cultivating is performed after a suitable time (e.g., after or after at least about 30-90 days, or after or after at least about 90-180, or after 365 days) for the soil to become a suitable cultivation medium.

The organism whose growth is controlled can be any unwanted or undesirable organisms, such as organisms causing harm to crops or plants. These organisms include, but are not limited to, insects, nematodes, fungi, and undesired vegetation. The term "undesired vegetation" denotes non-crop plant species that otherwise tend to grow in the areas where crops are planted, and includes both volunteer crops, plants that have previously been planted into soil and that can interfere with new or re-planted crops, and weeds. Typical weeds to be controlled include those associated with common annual or perennial crops including but not limited to those of the genus *Vitis, Fragaria, Juglans*, or *Prunus*.

The growth of any type of weed can be controlled using the method of the present invention. For example, weeds include barnyard grass, Bermuda grass, bindweed, burdock, chickweed, common purslane, crabgrass, dandelion, goldenrod, goosegrass, hairy nightshade, kudzu, milk thistle, mallow, morning-glory, pigweeds, poison ivy, purple nut sedge, ragweed, sicklepod, sorrel, shepherd's-purse, sow thistle, St. John's wort, sumac, teaweed, white goosefoot, and yellow nutsedge. In some embodiments, the weed can be at least one of yellow nutsedge, crabgrass, teaweed, sicklepod, or morning-glory. In other embodiments, the weed can be purple nutsedge.

In some cases, the undesired vegetation includes previously planted perennial crops. For example, perennial crops can be planted and replaced by the same or different crop after a number of years or decades. In some cases, the previously planted crop can be removed by conventional mechanical or herbicidal means, but latent roots in the cultivation medium can re-emerge. In some cases, methods described herein for controlling growth, viability, or survival of previously planted crops, can include a step of killing roots of said previously planted crops in the cultivation medium. In some cases, such methods can further include a step of debilitating root structure in the target cultivation medium before applying the pre-plant biocide (e.g., aqueous HyCyn) to the cultivation medium. In some cases, such methods can further include a step of debilitating root structure in the target cultivation medium after applying the pre-plant biocide (e.g., aqueous HyCyn) to the cultivation medium. For example, tilling or application of herbicides can be used to debilitate root structure. In such cases, the debilitating step may be performed during a period of time in which the pre-plant biocide (e.g., aqueous HyCyn) or biocidal metabolites thereof are still active in the cultivation medium. Thus, the debilitating can be performed, e.g., 1, 2, 3, 4, 5, 6, 7, 8, 9, 10, 11, 12, 13, 14, 15, 16, 17, 18, 19, 20, 21, 22, 23, 24, 25, 26, 27, or 28 days after pre-plant biocide (e.g., aqueous HyCyn) application. In some cases, the debilitating is performed from 1 to 28 days, from 2 to 28 days, from 3 to 28 days, from 4 to 28 days, from 6 to 28 days, or from 1 to 2 weeks after pre-plant biocide (e.g., aqueous HyCyn) application.

Other organisms whose growth can be controlled by the method of the present invention include pathogenic nematodes. Pathogenic nematodes that are deleterious to crop growth are plant-parasitic (e.g., endo or ectoparasitic) nematodes that include reniform nematodes (e.g., *Rotylenchulus reniformis*), spiral nematodes (e.g., *Helicotylenchus dihystera*), root-knot nematodes (e.g., *Meloidogyne arenaria, M. naasi, M. incognita*, or combination thereof), stubby root nematodes (e.g., *Paratrichodorus minor*), stunt nematodes (e.g., *Tylenchorhynchus claytoni*), lance nematodes (*Hoploloaimus*), root lesion nematodes (e.g., *Pratylenchus vulnus*), pin nematode (e.g., *Paratylenchus hamatus*), dagger nematodes (e.g., *Xiphinema* spp.), cyst nematodes (e.g., *Globodera* spp. or *Heterodera* spp.), and others, including combinations thereof. In some embodiments, the pathogenic nematode can be *Rotylenchulus reniformis*. The nematodes can be eggs, cysts, juveniles, dauer larva, or a combination thereof. Representative organisms to be controlled include weeds and pathogenic nematodes. In some embodiments, the organism can be a weed or a pathogenic nematode.

In some cases, methods described herein for controlling growth, viability, or survival of pathogenic nemotodes, such as one or more of the endoparasitic nematodes described herein, can include a step of debilitating root structure in the target cultivation medium. For example, tilling or application of herbicides can be used to enable delivery of pre-plant biocide (e.g., aqueous HyCyn) to (e.g., endoparasitic) nematodes to facilitate efficient killing of target organism. The debilitating can be performed before or after pre-plant biocide (e.g., aqueous HyCyn) application to the cultivation medium. In some cases, the debilitating step may be performed after pre-plant biocide (e.g., aqueous HyCyn) application but during a period of time in which the pre-plant biocide (e.g., aqueous HyCyn) or biocidal metabolites thereof are still active in the cultivation medium. Thus, the debilitating can be performed, e.g., 1, 2, 3, 4, 5, 6, 7, 8, 9, 10, 11, 12, 13, 14, 15, 16, 17, 18, 19, 20, 21, 22, 23, 24, 25, 26, 27, or 28 days after pre-plant biocide (e.g., aqueous HyCyn) application. In some cases, the debilitating is performed from 1 to 28 days, from 2 to 28 days, from 3 to 28 days, from 4 to 28 days, from 6 to 28 days, or from 1 to 2 weeks after pre-plant biocide (e.g., aqueous HyCyn) application.

Other organisms whose growth can be controlled by the method of the present invention include pathogenic fungi. Pathogenic fungi that are deleterious to crop growth include *Sclerotinia minor, Sclerotinia major, Fusarium* spp., *Verticillium dahliae*, or pathogenic fungi from the genera *Trichoderma* or *Fusarium* and others, including combinations thereof. In some embodiments, the pathogenic fungus can be *Fusarium*. Representative organisms to be controlled include weeds, pathogenic nematodes, and pathogenic fungi. In some embodiments, the organism can be a weed, a pathogenic nematode, or a pathogenic fungus. In some cases, for treatment or prevention of infections by pathogenic fungi, the pre-plant biocide can be applied to the cultivation medium (e.g., by drenching) at 3,000 ppm; 4,000 ppm; 5,000 ppm; 6,000 ppm; 7,000 ppm; 8,000 ppm; 9,000 ppm; 10,000 ppm, or higher. In some cases, the pre-plant biocide is applied to the surface, or only to the surface, of the planting bed. For example, the pre-plant biocide can be applied to 25%, 50%, 75%, or more of the planting bed surface, or the entire planting bed surface. In some cases, the pre-plant biocide, e.g., aqueous HyCyn, is applied (e.g., by drenching) in sufficient volume to penetrate to the tilling depth. In some cases, the pre-plant biocide is applied (e.g., by drenching) to the surface 1 inch, 2 inches, 3 inches, 4 inches, 5 inches, 6 inches, 7 inches, 8 inches, 10 inches, 12 inches, 14 inches, 18 inches, or more of the planting bed.

In some embodiments, the present invention provides a method for preparing a cultivation medium for a plant or a re-plant using a pre-plant biocide (e.g., to kill old trees/vines or roots thereof, kill associated nematodes inside or outside the roots, and/or remedy the root rejection component of the replant problem). In some embodiments, the method includes: i) contacting a cultivation medium with the pre-plant biocide containing water and hydrogen cyanamide or other water-soluble low molecular weight cyanamide or nitrile containing compound at a concentration of 400 to 10,000 ppm, thereby applying the pre-plant biocide. In some cases, the contacting is performed prior to planting or re-planting (e.g., from 30 to 90 days, or 30 to 365 days, or more, prior to planting or re-planting). In some embodiments, the concentration of water-soluble low molecular weight cyanamide or nitrile containing compound, e.g., hydrogen cyanamide, in the pre-plant biocide applied to the cultivation medium is, or is at least about, 400; 500; 600; 700; 750; 800; 900; 1,000; 2,000; 3,000; 4,000; 5,000; 6,000; 7,000; 8,000; 9,000; or 10,000 ppm.

In some embodiments, the method includes: i) contacting a cultivation medium with the pre-plant biocide containing water and hydrogen cyanamide or other water-soluble low molecular weight cyanamide or nitrile containing compound at a concentration of 400 to 10,000 ppm, thereby applying the pre-plant biocide; ii) waiting from 30 to 90 days, or 30 to 365 days, or more, after the contacting the cultivation medium with the pre-plant biocide; and iii) after the waiting, planting the plant into the cultivation medium. In some embodiments, the concentration of water-soluble low molecular weight cyanamide or nitrile containing compound, e.g., hydrogen cyanamide, in the pre-plant biocide applied to the cultivation medium is, or is at least about, 400; 500; 600; 700; 750; 800; 900; 1,000; 2,000; 3,000; 4,000; 5,000; 6,000; 7,000; 8,000; 9,000; or 10,000 ppm.

In some embodiments, the present invention provides a method for preparing a cultivation medium for growing a plant or re-plant using a pre-plant biocide. In some embodiments, the method includes: i) contacting a cultivation medium with the pre-plant biocide containing, e.g., aqueous hydrogen cyanamide, at a concentration of 400 to 10,000 ppm, thereby applying the pre-plant biocide, wherein the contacting is performed prior to planting or re-planting (e.g., from 30 to 90 days, or 30 to 365 days, or more, prior to planting or re-planting). In some embodiments, the present invention provides a method for growing a plant or re-plant using a pre-plant biocide. In some embodiments, the method includes: i) contacting a cultivation medium with the pre-plant biocide at a concentration of 400 to 10,000 ppm, thereby applying the pre-plant biocide; ii) waiting from 30 to 90 days, or 30 to 365 days, or more, after the contacting the cultivation medium with the pre-plant biocide; and iii) after the waiting, planting the plant into the cultivation medium. In some embodiments, the concentration of water-soluble low molecular weight cyanamide or nitrile containing compound, e.g., hydrogen cyanamide, in the pre-plant biocide applied to the cultivation medium is, or is at least about, 400; 500; 600; 700; 750; 800; 900; 1,000; 2,000; 3,000; 4,000; 5,000; 6,000; 7,000; 8,000; 9,000; or 10,000 ppm.

In some embodiments, the present invention provides a method for growing a plant using a pre-plant biocide, the method including: i) irrigating a cultivation medium to at least about 5% water saturation (e.g., 5%, 10%, 20%, 25%, 30%, or 40% saturation); ii) after the irrigating, contacting the cultivation medium with the pre-plant biocide containing, e.g., aqueous hydrogen cyanamide, at a concentration of 400 to 10,000 ppm, thereby applying the pre-plant biocide; iii) waiting from 30 to 90 days, or 30 to 365 days, or more, after the contacting the cultivation medium with the pre-plant biocide; and iv) after the waiting, planting the plant into the cultivation medium. In some embodiments, the present invention provides a method for preparing a cultivation medium for growing a plant using a pre-plant biocide, the method including: i) irrigating a cultivation medium to at least about 5% water saturation (e.g., 5%, 10%, 20%, 25%, 30%, or 40% saturation); ii) after the irrigating, contacting the cultivation medium with the pre-plant biocide containing, e.g., aqueous hydrogen cyanamide, at a concentration of 400 to 10,000 ppm, thereby applying the pre-plant biocide, wherein the contacting is performed prior to planting (e.g., from 30 to 90 days, or 30 to 365 days, or more, prior to planting). In some embodiments, the concentration of water-soluble low molecular weight cyanamide or nitrile containing compound, e.g., hydrogen cyanamide, in the pre-plant biocide applied to the cultivation medium is, or is at least about, 400; 500; 600; 700; 750; 800; 900; 1,000; 2,000; 3,000; 4,000; 5,000; 6,000; 7,000; 8,000; 9,000; or 10,000 ppm.

In some embodiments, the present invention provides a method for growing a plant using a pre-plant biocide, the method including: i) irrigating a cultivation medium to a greater than 50% water saturation level; ii) after the irrigating, allowing the irrigated cultivation medium to drain to a saturation level of 50%-25%; iii) contacting the cultivation medium with the pre-plant biocide containing, e.g., aqueous hydrogen cyanamide, at a concentration of 400 to 10,000 ppm, thereby applying the pre-plant biocide; iv) waiting from 30 to 90 days, or 30 to 365 days, or more, after the contacting the cultivation medium with the pre-plant biocide; and v) after the waiting, planting the plant into the cultivation medium. In some embodiments, the present invention provides a method for preparing a cultivation medium for growing a plant using a pre-plant biocide, the method including: i) irrigating a cultivation medium to a greater than 50% water saturation level; ii) after the irrigating, allowing the irrigated cultivation medium to drain to a saturation level of 50%-25%; and iii) contacting the cultivation medium with the pre-plant biocide containing, e.g., aqueous hydrogen cyanamide, at a concentration of 400 to 10,000 ppm, thereby applying the pre-plant biocide, wherein the contacting is performed prior to planting (e.g., from 30 to 90 days, or 30 to 365 days, or more, prior to planting). In some embodiments, the concentration of water-soluble low molecular weight cyanamide or nitrile containing compound, e.g., hydrogen cyanamide, in the pre-plant biocide applied to the cultivation medium is, or is at least about, 400; 500; 600; 700; 750; 800; 900; 1,000; 2,000; 3,000; 4,000; 5,000; 6,000; 7,000; 8,000; 9,000; or 10,000 ppm.

In some embodiments, the pre-plant biocide is applied (e.g., drenched) in a field wherein older trees or vines have received their final harvest, soil temperatures exceed 15° C. and the method comprises: i) construction of basins for each tree in sloping land or each row of trees/vines in flat land; ii) saturating the soil in each basin with water; iii) contacting the cultivation medium with the pre-plant biocide containing, e.g., aqueous hydrogen cyanamide, at a concentration of 1,000-2,000 ppm; iv) waiting 30 to 360 days during which old trunks are sawn at medium surface after the contacting; and v) after the waiting, planting the plant into the cultivation medium, wherein: a) the applying the pre-plant biocide reduces 90-99.9% of endoparasitic nematodes in old roots, endo and endoparasitic nematodes from a zone as deep and wide as new roots expand in the first year, b) the applying the pre-plant biocide reduces a number of viable weeds in the cultivation medium by at least 50-99.9% at the time of replanting relative to an untreated control cultivation medium, and c) the applying the pre-plant biocide plus planting a rootstock of different species can completely reduce the root rejection component of the replant problem (see, McKenry 1999) and provide, augment, or protect nematode resistance mechanisms within the new rootstock.

In some embodiments, the pre-plant biocide is applied (e.g., drenched) in a tilled coarse-textured soil to be planted with annual crops, wherein the soil is infested with pathogenic nematodes and soil temperatures exceed 15° C., the method compromising: i) constructing shallow basins or laying of high flow drip lines or blankets with about 0.5 to about 5 gal/hr (e.g., 1 gal/hr) emitters placed at each 8 inches along and across the field surface or use of low mist micro-sprinklers elevated just above a recently saturated field surface or formed bed; ii) contacting the cultivation medium with a pre-plant biocide comprising water and hydrogen cyanamide at 1,000 to 2,000 ppm; and iii) waiting 15 to 60 days to plant new plants, seeds or transplants into the cultivation medium, wherein: a) the applying the pre-plant biocide reduces pathogenic nematode populations by 90 to 99.9% within a treated 10-24 inch depth of cultivated medium at the time of planting relative to an untreated control of the cultivation medium; b) the applying of the pre-plant biocide reduces viable weed populations by 50-99.9% relative to an untreated control cultivation medium; and c) fungal propagules and newly planted seeds or transplants are not damaged by the 1,000-1,500 ppm pre-plant biocide.

In some embodiments, the pre-plant biocide is applied (e.g., drenched) in a tilled coarse-textured soil to be planted with annual crops, wherein the soil is infested with fungal pathogens in the surface 2-4 inches at soil temperatures from 10-35° C., 4,000 to 6,000 ppm hydrogen cyanamide solution can be delivered as described herein, e.g., as drenched zones from field surface to 3-inch depth, or from field surface to 14 inches of depth. In some embodiments, the fungal pathogen is *Sclerotinia* or *Sclerotium*.

In some embodiments, the pre-plant biocide provides carbon and nitrogen metabolites in the cultivation medium to existing plants or future plants. In some cases, the pre-plant biocides described herein, such as the soil metabolizable formulations, when applied during treatment can provide a lasting supply of available nitrogen to the soil (see, US 2016/0073639). In some cases, removal and replanting of perennial crops can be improved using pre-plant biocides described herein (e.g., aqueous HyCyn), which can be applied after a final harvest and before re-planting to rid a field of root rejections, nematodes in and out of old roots, weed seeds and provide a full year supply of available for initiating new growth.

In some embodiments, (a) the applying the pre-plant biocide reduces a number of viable pathogenic nematodes in the root zone of the cultivation medium by at least about 90% (e.g., at least about 93%) to a depth of from about 1 to about 5 feet (e.g., 4 feet) at the time of planting relative to an untreated control cultivation medium. In some embodiments, (b) the applying the pre-plant biocide reduces a number of viable weeds in the cultivation medium by at least about 90%, 95%, or 99% at the time of planting relative to an untreated control cultivation medium. In some embodiments, (c) the applying the pre-plant biocide reduces a number of viable pathogenic fungal organisms in the cultivation medium by at least about 90% at the time of planting relative to an untreated control cultivation medium. In some embodiments, the method provides the foregoing (a) and (b); (a) and (c); (b) and (c); or (a), (b), and (c).

In some embodiments, the applying the pre-plant biocide reduces a number of viable pathogenic nematodes in the root zone of the cultivation medium by at least about 90% (e.g., at least about 93%) to a depth of from about 1 to about 5 feet (e.g., 4 feet) for 30-60 days, 30-90 days, 30-365 days, or more, after planting relative to an untreated control cultivation medium. In some embodiments, the applying the pre-plant biocide reduces a number of viable pathogenic nematodes in the root zone of the cultivation medium by at least about 90% (e.g., at least about 93%) to a depth of from about 1 to about 5 feet (e.g., 4 feet) for more than 60 days after planting relative to an untreated control cultivation medium. In some embodiments, the applying the pre-plant biocide reduces a number of viable pathogenic nematodes in the root zone of the cultivation medium by at least about 90% (e.g., at least about 93%) to a depth of from about 1 to about 5 feet (e.g., 4 feet) for at least 1 year after planting relative to an untreated control cultivation medium.

In some embodiments, i) includes irrigating the cultivation medium to a greater than 55%, 60%, 65%, 70%, 75%, 80%, 85%, 90%, 95%, or 99% water saturation level. In some embodiments, i) includes irrigating the cultivation medium to saturation. In some embodiments, ii) includes after the irrigating, allowing the irrigated cultivation medium to drain to a saturation level of 50%, 45%, 40%, 35%, 30%, 25%, or 20%. Drainage to any one or more of the foregoing saturation levels typically can be performed in an agricultural field by waiting from 1 to 10 days (e.g., 1, 2, 3, 4, 5, 6, 7, 8, 9, or 10 days).

In some embodiments, the waiting after the contacting of the pre-plant biocide and before planting the plant is performed for, or for at least about, 14, 15, 16, 17, 18, 19, 20, 21, 22, 23, 24, 25, 26, 27, 28, 29, or 30 days. In some cases, the waiting is performed for, or for at least about, 14 to 28 days; 30 to 60 days; 30 to 90 days; or 60 to 90 days. Typically, the waiting period is selected to coincide with a level of un-metabolized biocide that is non-toxic, or substantially non-toxic, to the plant to be planted.

In some embodiments, the contacting includes applying the pre-plant biocide to the cultivation medium (e.g., by drenching) to a depth of, or of at least; 1-10 inches (e.g., 1, 2, 3, 4, 5, 6, 7, 8, 9, or 10 inches); or a depth of, or of at least 1-4 or 5 feet (e.g., 1, 2, 3, 4, or 5 feet). In some embodiments, the cultivation medium is tilled soil (e.g., well-tilled soil), and the contacting includes drenching the cultivation medium to the tilling depth. Generally, the pre-plant biocide is delivered to a volume of cultivation medium where the control is desired. For example, if the organism to be controlled is a pathogenic fungus, such as *Fusarium* spp. or *Sclerotinia* spp., then a relatively shallow delivery (e.g., drenching of the first 1, 2, 3, 4, 5, 6, 7, 8, 9, or 10 cm of cultivation medium) can be effective. As another example, drenching a pre-plant biocide to a depth of 1, 2, 3, 4, or 5 feet, or more, can be effective for long-lasting effective control of pathogenic nematodes in a zone around a perennial plant. In some cases, such targeted pre-plant biocide delivery provides a treated area with a reduction in or elimination of weeds, or fungal and/or nematode pathogens. In some cases, this treated zone allows the plant (e.g., seed, seedling, rooting, etc.) to grow for a period of time in a reduced pathogen or pathogen free environment until the root zone exceeds the boundaries of the treated zone.

In some embodiments, the pre-plant biocide containing, e.g., aqueous hydrogen cyanamide, is a soil metabolizable biocide solution. In some embodiments, the soil metabolizable biocide solution contains hydrogen cyanamide, in an amount of from about 0.1% to about 20% (w/w); a polyhydroxy organic compound soluble in water, in an amount of from about 10% to about 90% (w/w); and water to 100%. In some cases, the polyhydroxy compound is selected from the group consisting of glycerin, a sugar alcohol, ethylene glycol, propylene glycol, erythritol, xylitol, and mannitol, or a combination thereof.

In some embodiments, the applying the pre-plant biocide provides at least a one-year supply of available nitrogen to the plant. In some cases, the method of the present invention includes not applying to the cultivation medium an additional supply of available nitrogen within, or within at least, 1, 2, 3, 4, 5, 6, 7, 8, 9, 10, 11, or 12 months after planting the plant.

In some embodiments, applying the pre-plant biocide provides a 10% to a 600% improved first year growth benefit relative to a control plant planted in an untreated control cultivation medium. For example, the first year growth benefit can be, or can be at least, 10%, 20%, 30%, 40%, 50%, 60%, 70%, 80%, 100%, 120%, 150%, 175%, 200%, 300%, 400%, 500%, or 600%.

In some embodiments, the present invention provides a method of reducing root rejection by applying a pre-plant biocide to a cultivation medium. In some cases, the rate of root rejection is reduced relative to an untreated control cultivation medium by, or by at least, 10%, 25%, 50%, 75%, or 90%.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

EXAMPLES

The following examples are offered strictly for illustration and are not intended to limit the scope of the invention.

Example 1

In situ soil borne pest and disease populations were determined from known commercial locations. These infested soils were commonly of sandy loam or fine sandy loam texture that were screened free of all but the smallest of roots as they were placed into buckets. Buckets were then transported to a single location of deep loamy sand soil where 30" long by 3" diameter PVC open-ended pipes had been inserted to a depth of 22" using a 3" can auger (FIG. 1). Each soil column was then filled with infested soil to a depth of 22" using a shovel handle to compress soil density during the soil transfer process.

The surface 8" of each column remained vacant in order to eventually apply one liter of biocide solution onto each soil column and then determine the amount of time required to fully infiltrate the liter of water. Because infiltration rates varied from 3 hr to 4 days across each different biocide with or without adjuvant each column was used only once. Columns were cleaned and re-inserted to a different nearby location for subsequent tests. As testing proceeded dosage response curves were developed to reveal dosages needed to reach threshold levels for pest impact followed by quantification of the dosage needed to achieve as much as 100% pest kill where possible. These solutions were not benefited by use of various adjuvants as infiltration rates of the biocide solutions were similar to that of water. Results for the rate of nematode control with various biocide formulations are depicted in FIGS. 2-6.

Example 2

An orchard supporting six-year-old almond trees grafted onto NEMAGUARD® peach infested with *Pratylenchus vulnus* and *Paratylenchus hamatus* nematodes located near Parlier, Calif., provided a soil of interest. This soil had already received study to indicate that in addition to nematodes, the rejection component of the replant problem (McKenry, 1999), was associated with the soil ecosystem (Jiue-in Yang et al., 2012) so total bacteria and yeast cells/gram of soil were quantified to determine if the biocide possessed a gross capability to impact bacteria and/or yeasts. The soil dilution technique was used and followed by plating onto potato dextrose agar (PDA) for bacteria and acidified PDA for yeasts. Results are depicted in FIGS. 7 (bacteria, 14 DAT), 8 (bacteria, 28 DAT), 9 (yeast, 14 DAT), and 10 (yeast, 28 DAT). Nematodes were extracted from soil using sugar centrifugation and quantified per 250 cc soil samples collected at 14, 28, and 60 days after treatment (data not shown) using a 2" can auger. Samples were counted for each nematode species present.

Soil from two fields with a history of replanting strawberries near Andreas, C A, and Watsonville, Calif., was placed into soil columns and assessed for *Fusarium oxysporum*, total *Fusarium* spp. and *Verticillium dahlia*. Presence of *Verticillium* was assessed using pectate media after wet sieving of the soil and no propagules were present from any sample. For *Fusarium* spp. a soil dilution technique was employed followed by plating onto Komada's medium which is semi-selective for *F. oxysporum*. Soil samples were collected by 2" can auger at 14 days after treatment. Results are depicted in FIGS. 11 (Andreas, Calif.), and 12 (Watsonville, Calif.).

Soil was placed into soil columns, drenched with a range of biocide solutions and soil collected from columns using a 2" diameter can auger. Lab assessment of *Sclerotinia minor* and or *S. major* involved wet sieving of the soil using techniques of Hoes and Huang, 1975, and Dillard and Grogan, 1985. Viability of the sclerotia was then determined using the method of Subbaro et al., 1994. Counts of sclerotia and viable sclerotia were determined from soil collected at 14 days after treatment. Results are depicted in FIG. 13.

Counts of the various microbes were subjected to ANOVA then Duncan's Multiple Range test with a default cutoff of $p=0.05$ or a cutoff of $p=0.01$ where indicated.

Example 3

Silt soil at a temperature of 21° C. was prepared to be planted with strawberries as described herein. Soil columns were drenched with HyCyn at 3,000 ppm; 4,000 ppm; 5,000 ppm; 6,000 ppm; or water only to determine application rate to control *Fusarium oxysporum*, total *Fusarium* spp and total *Cylindrocarpon* spp. Soil was sampled at 30 and 70 days after treatment (DAT) from columns drenched to 56 cm depth. The results are depicted in FIGS. 14-17.

Field Station evaluations included sandy loam soil at 10° C. vs 15° C. in adjacent sites. These sites were uniformly infested with *Meloidogyne incognita* race-3. The first site (10° C.) was drenched with 750 or 1,000 ppm to a depth of 40 cm and planted with carrots 70 DAT. Ten weeks later soil at the second site (15° C.) was drenched with 1,250 or 1,500 ppm and 30 DAT planted with sweet potato slips. Nematode samples were collected at 0-15 and 15-30 cm depths. Lower treatment rates in cold (10° C.) soil provided no nematode control (FIG. 18), suggesting that a higher dose (e.g., 2,000 ppm, 4,000 ppm, or higher) may be necessary in colder soils. Moderate treatment rates in the warmer (15° C.) soil did provide nematode control (FIG. 19).

Field Station evaluation in sandy loam soil at 10° C. to be planted to cotton soil was drenched with 3,000 or 4,500 ppm HyCyn to 40 cm depth. *F. oxysporum* race-4 were identified and counted at 28 DAT (FIG. 20) and 70 DAT (FIG. 21). The highest rate was necessary to halt *F. oxysporum* but burning of leaves of cotton or occasional nutgrass did not cease even five months after treatment in this never irrigated field.

Figure 23:
FIG. 23: illustrates improved growth of a tree cultivated for six months in soil treated with 1,000 ppm HyCyn as compared to soil treated with 250 ppm Telone ec, or untreated soil.

Field Station evaluation involved sandy loam soil at an almond replant site drenched uniformly with 1,000 ppm. Surface soil was collected 60 days later and potted from three treatments, water only, 250 ppm Telone EC and 1000 ppm HyCyn. Young almond trees on NEMAGUARD rootstock were planted to each pot and trees maintained for six months. Within 2 months after planting the HyCyn trees showed improved growth as indicated in FIG. 22. At the $6^{th}$ month, plant biomass differences were greater following HyCyn compared to the untreated, as indicated in FIG. 23. HyCyn at 1,000 ppm provides a remedy for the root rejection component of the replant problem (McKenry, 1999).

Figure 24:
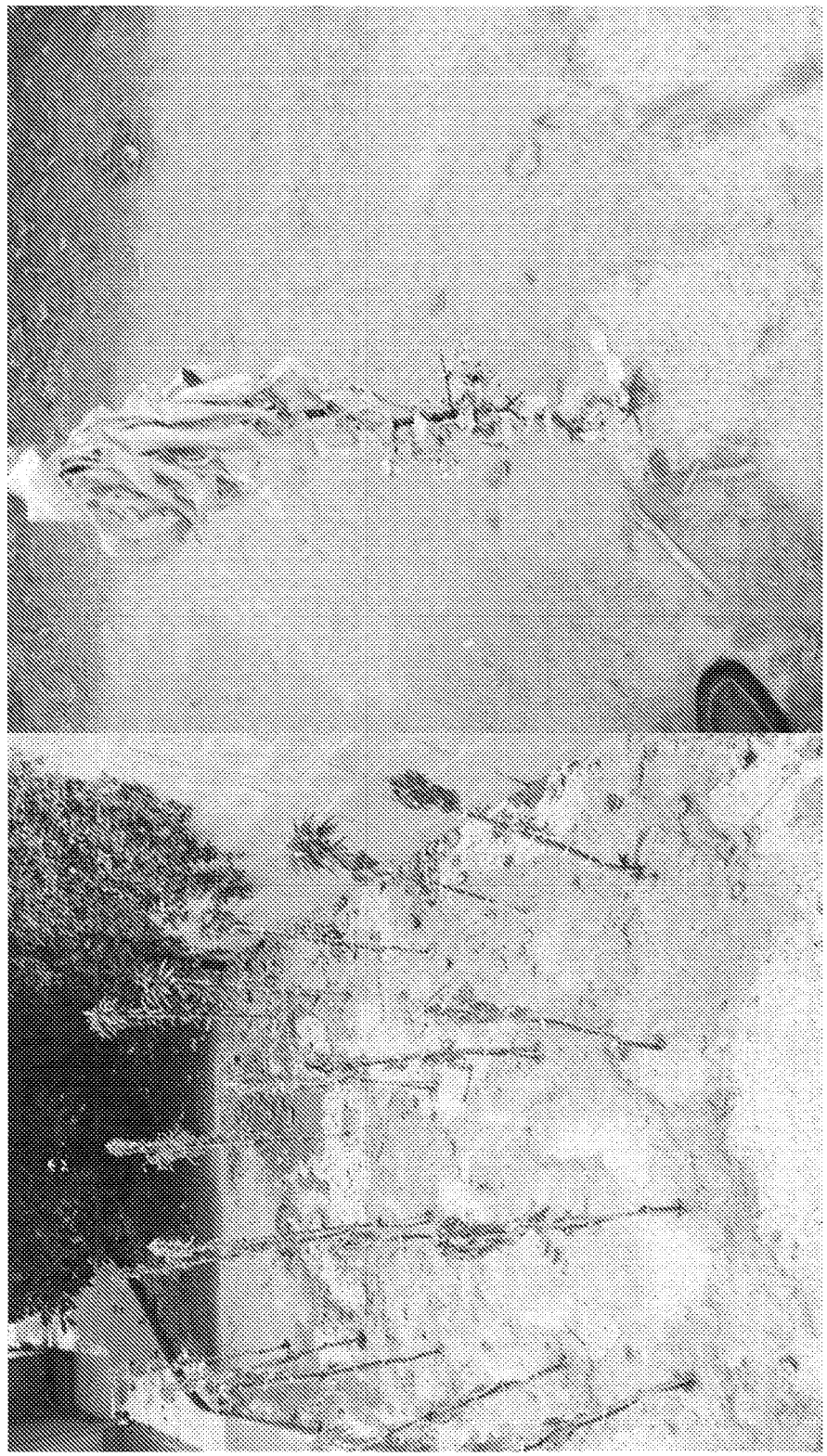
FIG. 24: illustrates results from drenching of 1 year old NEMAGUARD® peach root stocks at the indicated HyCyn concentrations (ck=0 ppm HyCyn). The drenching was performed for the indicated times. Left panel is 30 days after root drenching. Right panel is a close up of one survivor 60 days after 750 ppm for 18 hr.
Figure 25:
FIG. 25: illustrates treated survivors 60 DAT. The survivor on the left was treated at 750 ppm for 18 hr. The survivor in the middle was treated at 400 ppm for 6 hours. The survivor on the right was untreated.

Field Station evaluation where root systems of one-year-old almonds trees were placed in concentrations of HyCyn. Intact 1-yr-old trees were separated from their planting pots and placed into buckets containing open solutions of 400; 750; 1,000; 1,250; 1,500; or 3,000 ppm HyCyn for 6, 18 or 24 hr. Where entire root systems were soaked in a static setting 24 hr at 750 ppm no tree survived or re-initiated growth. The results are depicted in FIGS. 24 and 25.

Figure 26:
FIG. 26: illustrates results of treatment of 8-year old *Juglans cathayensis* trees with 2,000 ppm HyCyn in 400 or 800 L of water.

Field Station evaluation of eight-year-old butternut trees, *Juglans cathayensis*, drenched with 2,000 ppm HyCyn within 400 or 800 L water. Two of four trees receiving 400 L solution were not completely killed but four of four trees receiving 800 L of the same solution were killed (FIG. 26). A five-day sieve-mist extraction of all nematodes from roots and soil revealed kill of all *P. vulnus* from root samples plus 99.9% kill of soil dwelling nematodes beneath the surface 90 cm of treated soil (FIG. 27).

Counts of the various microbes were subjected to ANOVA then Duncan's Multiple Range test with a default cutoff of p=0.05 or a cutoff of p=0.01 where indicated.

REFERENCES

Dillard, H. R, and Grogan, R. G. (1985), Phytopathology, 75:90-94.
Hoes, J. A. and Huang, H. C. (1975), Phytopathology 65:1431-1432.
Jiue-in Yang et al., (2012) PloS ONE 7(10): e46420
McKenry, M. V (1999) UC KARE available at kare.ucanr.edu/files/86495.pdf
Subbaro, K. V. et al., (1994), Phytopathology 84:1471-1475.

What is claimed is:

1. A method for using a pre-plant biocide to prepare a cultivation medium for growing a plant, the method comprising:
   i) irrigating an unplanted cultivation medium to a greater than 50% water saturation level;
   ii) after the irrigating, allowing the irrigated cultivation medium to drain to a saturation level of 50%-25%; and
   iii) contacting the cultivation medium with the pre-plant biocide comprising water and hydrogen cyanamide at a concentration of 600-10,000 ppm, thereby uniformly applying the pre-plant biocide, wherein the contacting is performed 30 to 90 days prior to a time of planting the plant;
   and wherein:
      (a) the applying the pre-plant biocide reduces a number of viable pathogenic nematodes in the root zone of the cultivation medium by at least about 90% to a depth of 4 feet at the time of planting relative to an untreated control cultivation medium;
      (b) the applying the pre-plant biocide reduces a number of viable weeds in the cultivation medium by at least about 99% at the time of planting relative to an untreated control cultivation medium; or
      (c) the applying the pre-plant biocide reduces a number of viable pathogenic fungal organisms in the cultivation medium by at least about 90% at the time of planting relative to an untreated control cultivation medium.

2. The method of claim 1, wherein:
   (a) the applying the pre-plant biocide reduces the number of viable pathogenic nematodes in the root zone of the cultivation medium by at least about 93% to a depth of 4 feet at the time of planting relative to an untreated control cultivation medium; and
   (b) the applying the pre-plant biocide reduces the number of viable weeds in the cultivation medium by at least about 99% at the time of planting relative to an untreated control cultivation medium.

3. The method of claim 1, wherein:
   (a) the applying the pre-plant biocide reduces the number of viable pathogenic nematodes in the root zone of the cultivation medium by at least about 93% to a depth of 4 feet at the time of planting relative to an untreated control cultivation medium;
   (b) the applying the pre-plant biocide reduces the number of viable weeds in the cultivation medium by at least about 99% at the time of planting relative to an untreated control cultivation medium; and
   (c) the applying the pre-plant biocide reduces the number of viable pathogenic fungal organisms in the cultivation medium by at least about 90% at the time of planting relative to an untreated control cultivation medium.

4. The method of claim 1, wherein the contacting comprises drenching the cultivation medium to a depth of 1-10 inches.

5. The method of claim 1, wherein prior to the contacting, the cultivation medium is tilled to a specified tilling depth, and the contacting comprises drenching the cultivation medium to the tilling depth.

6. The method of claim 1, wherein the pathogenic nematodes are at an egg, cyst, or juvenile life cycle stage.

7. The method of claim 1, wherein the pathogenic nematodes are in a dauer larva life cycle stage.

8. The method of claim 1, wherein the pathogenic nematodes are selected from the group consisting of *Meloidogyne* spp., *Pratylenchus vulnus*, *Paratylenchus hamatus*, *Rotylenchulus reniformis*, and *M. xenoplax*.

9. The method of claim 1, wherein the pathogenic fungi is selected from the group consisting of *Sclerotinia minor*, *Sclerotinia major*, *Fusarium* spp., *Verticillium dahliae*, and pathogenic fungi from a genus *Trichoderma* or a genus *Fusarium*.

10. The method of claim 1, wherein the weeds are selected from the group consisting of *Capsella bursa-pastoris*, *Solanum sarrachoides*, *Sonchus* spp., *Portulaca oleraceae*, *Amaranthus* spp., *Chenopodium album*, *Malva* spp., *Cyperus rotundus*, *Cyperus esculentus*, *Ipomoea hederacea*, *Ipomoea lacunosa*, *Senna obtusifolia*, *Digitaria sanguinalis*, and *Eleusine indica*, or a combination thereof.

11. The method of claim 1, wherein the pre-plant biocide comprising water and hydrogen cyanamide is a soil metabolizable biocide solution.

12. The method of claim 11, wherein the soil metabolizable biocide solution comprises hydrogen cyanamide, in an amount of from about 0.1% to about 20% (w/w); a polyhydroxy organic compound soluble in water, in an amount of from about 10% to about 90% (w/w); and water to 100%.

13. The method of claim 12, wherein the polyhydroxy compound is selected from the group consisting of glycerin, a sugar alcohol, ethylene glycol, propylene glycol, erythritol, xylitol, and mannitol.

14. The method of claim 11, wherein the applying the pre-plant biocide provides at least a one-year supply of available nitrogen to the plant.

15. The method of claim 1, wherein the plant is of the genus *Vitis, Fragaria, Juglans*, or *Prunus*.

16. The method of claim 1, wherein the applying the pre-plant biocide provides a 10% to a 600% improved first year growth benefit relative to a control plant planted in an untreated control cultivation medium.

17. The method of claim 1, wherein the applying the pre-plant biocide reduces a number of viable pathogenic nematodes in the root zone of the cultivation medium by at least about 93% to a depth of 4 feet for 30-60 days after planting relative to an untreated control cultivation medium.

18. The method of claim 1, wherein the applying the pre-plant biocide reduces a number of viable pathogenic nematodes in the root zone of the cultivation medium by at least about 93% to a depth of 4 feet for more than 60 days after planting relative to an untreated control cultivation medium.

19. The method of claim 1, wherein the applying the pre-plant biocide reduces a number of viable pathogenic nematodes in the root zone of the cultivation medium by at least about 93% to a depth of 4 feet for at least 1 year after planting relative to an untreated control cultivation medium.

20. A method of planting a plant in a cultivation medium, the method comprising:
   providing a cultivation medium prepared with a pre-plant biocide according to the method of claim 1; and
   planting the plant.

* * * * *